US00RE44401E

(19) United States
(12) Reissued Patent
Soldin

(10) Patent Number: US RE44,401 E
(45) Date of Reissued Patent: Jul. 30, 2013

(54) THYROID HORMONE ANALYSIS BY MASS SPECTROMETRY

(75) Inventor: Steven J. Soldin, Bethesda, MD (US)

(73) Assignee: Georgetown University, Washington, DC (US)

(21) Appl. No.: 13/298,663

(22) Filed: Nov. 17, 2011

Related U.S. Patent Documents

Reissue of:
(64) Patent No.: 7,618,827
Issued: Nov. 17, 2009
Appl. No.: 10/823,690
Filed: Apr. 14, 2004

U.S. Applications:
(60) Provisional application No. 60/462,745, filed on Apr. 14, 2003.

(51) Int. Cl.
*G01N 33/53* (2006.01)
*G01N 33/00* (2006.01)

(52) U.S. Cl.
USPC ..... 436/173; 436/500; 422/50; 422/430

(58) Field of Classification Search
USPC ..... 436/173
See application file for complete search history.

(56) References Cited

U.S. PATENT DOCUMENTS 4,741,897 A * 5/1988 Andrews et al. ..... 436/500
2004/0235188 A1* 11/2004 Soldin ..... 436/500

FOREIGN PATENT DOCUMENTS

WO WO 01/88548 * 11/2001
WO 0246772 A 6/2002
WO WO 0246772 * 6/2002

OTHER PUBLICATIONS

Soukhova, N. et al., "Isotope Dilution Tandem Mass Spectrometric Method for T4/T3" Clinica Chimica Acta, Elsevier BV, Amsterdam, NL, vol. 343, No. 1/02, Jan. 1, 2004, pp. 185-190.*
Gu Jianghong et al. "Simultaneous quantification of free triiodothyronine and free thyroxine by isotope dilution tandem mass spectrometry", Dec. 2007, Clinical Biochemistry, vol. 40, NR. 18, pp. 1386-1391.*
International Search Report for PCT/US 05/38232 dated Sep. 13, 2007.*
European Search Report for EP 05 85 1243 dated Mar. 11, 2009.*
Siekmann, L., "Measurement of thyroxine in human serum by isotope dilution mass spectrometry. Definitive methods in clinical chemistry, V", Biomedical and Environmental Mass Spectrometry, vol. 14, No. 11, Nov. 1987, pp. 683-688.*
Thienpont, L.M., et al., "Development of a new method for the determination of thyroxine in serum based on isotope dilution gas chromatography mass spectrometry", Biol Mass Sprectrom, vol. 23, No. 8, 1994, pp. 475-482.*
De Brabandere, Vi et al., "Isotope dilution-liquid chromatography/electrospray ionization-tandem mass spectrometry fo~ the determination of serum thyroxine as a potential reference method", Rapid Commun Mass Spectrom, vol. 12, No. | 16, 1998, pp. 1099-1103.|*
Kosaka, Takeo et al., "Analysis of thyroid hormones in health foods by LC/MS" Shokuhin Eiseigaku Zasshi, vol. 43, No. 4, Aug. 2002, pp. 225-229.*
Tai, SSC et al., "Candidate reference method for total thyroxine in human serum: use of isotope dilution liquid chromatography-mass spectrometry with electrospray ionization", Clinical Chemistry, vol. 48, No. 4, 2002, pp. 637-642.*
Chang, Y-C et al., "Quantitative measurement of male steroid hormones using automated on line solid phase extraction liquid chromatography tandem mass spectrometry and comparison with radioimmunoassay", Analyst, vol. 128, No. 4, Apr. 1, 2003, pp. 363-368.*
International Search Report for PCT/CA2004/000555, dated Jul. 2, 2004.*
Draisci, R. et al, Quantitation of anabolic hormones and their metabolites in bovine serum and urine by liquid chromatography-tandem mass spectrometry, 2000, Journal of Chromatography A, 870, 511-522.*
Thienpone Linda M. et al., Isotope Dilution-Gas Chromatography/Mass Spectrometry and Liquid Chromatography/Electrospray Ionization-Tandem Mass Spectrometry for the Determination of Triiodo-L-Thyronine in Serum, 1999, Rapid Communications in Mass Spectroscopy, 13, 1924-1931.*
Kissmeyer, Anne-Marie et al., Determination of the vitamin D analog EP 1089 (seocalcitol) in human and pig serum using liquid chromatography-tandem mass spectrometry, 2000, Journal of Chromatography B, 740, 117-128.*
Jonsson, Bo A.G., et al., Determination of cotrisol in human saliva using liquid chromatography-electrospray tandem mass spectrometry, 2003, Joumal of Chromatography B, 784, 63-68.*
Leinonen, Antti, et al., Liquid chromatography/mass spectrometry in steroid analysis-optimization and comparison of three ionization techniques: electrospray ionization, atmospheric pressure chemical ionization and atmospheric pressure photoionization, 2002, Journal of Mass Spectrscopy, 37, 693-698.*
Fredline, Victoria F et al., A Reference Method for the Analysis of Aldosterone in Blood by High-Performance Liquid Chromatography-atmospheric Pressure Chemical Ionization-TandemMass Spectrometry, 1997, Analytical Biochemistry, 252, 308-313.*
Vogeser, Michael et al., Determination of Serum cotrisol by Isotope-Dilution Liquid-Chromatography Electrospray Ionization tandem Mass Spectrometry with On-line Extraction, 2001, Clin Chem Lab, 39(10), 944-947.*

* cited by examiner

*Primary Examiner* — Christine T Mui
(74) *Attorney, Agent, or Firm* — McCarter & English, LLP

(57) ABSTRACT

Methods, systems and kits for the simultaneous or sequential analysis of one or more hormones by mass spectrometry are disclosed. The methods require minimal sample size and minimal preparation time. The methods include ionizing the hormones and analyzing the hormones by mass spectrometry. In addition, methods, systems and kits for the simultaneous or sequential analysis of thyroid hormones are disclosed including ionization of the thyroid hormones in the negative mode using an electrospray source.

60 Claims, 5 Drawing Sheets

Tandem mass spectrometric chromatogram for a plasma sample.
T4 m/z (776/127); $D_2T4$ m/z (778/127); T3 m/z (650/127).

T3 measured by Isotope dilution tandem mass spectrometry vs. immunoassay. IA = 0.75 MS + 0.21; r = 0.848; $S_{y.x}$ = 0.1956; n = 49

T4 measured by isotope dilution tandem mass spectrometry vs. immunoassay. IA = 1.13 MS – 8.99; r = 0.931; $S_{y.x}$ = 9.54; n=50

THYROID HORMONE ANALYSIS BY MASS SPECTROMETRY

Matter enclosed in heavy brackets [ ] appears in the original patent but forms no part of this reissue specification; matter printed in italics indicates the additions made by reissue.

*CONTINUING DATA*

*This is an application that is a Reissue of U.S. application Ser. No. 10/823,690 filed Apr. 14, 2004 which is now U.S. Pat. No. 7,618,827, which claims benefit of U.S. Provisional Patent Application No. 60/462,745, filed Apr. 14, 2003, each of which is incorporated herein by reference in its entirety.*

FIELD OF THE INVENTION

The present invention combines the fields of hormone analysis and mass spectrometry. In particular the invention relates to analyzing thyroid hormones using mass spectrometry.

BACKGROUND OF THE INVENTION

Hormones are biological messengers. They are synthesized by specific tissues (glands) and are secreted into the blood. The blood carries them to target cells where they act to alter the activities of the target cells.

Hormones are chemically diverse, and are generally categorized into three main groups: (1) small molecules derived from amino acids, for example thyroxine, (2) polypeptides or proteins, for example insulin and thyroid-stimulating hormone, and (3) molecules derived from cholesterol, for example steroids.

An important class of hormone is the thyroid hormones. Examples of thyroid hormones are thyroxine (T4), free thryoxine (FT4) and triiodothyronine (T3). T4 and T3 enter cells and bind to intracellular receptors where they increase the metabolic capabilities of the cell by increasing mitochondria and mitochondrial enzymes. T4 and T3 are important in regulating a number of biological processes, including growth and development, carbohydrate metabolism, oxygen consumption, protein synthesis and fetal neurodevelopment. Synthesis of all circulating T4 and a small percentage of circulating T3 occurs on thyroglobulin molecules located within the thyroid. The bulk of the T3 present in the blood is produced enzymatically via monodeiodination of T4 by specific intracellular deiodinases—enzymes present in the follicular cells and the cells of target tissues [1]. In serum drawn from healthy human subjects, total T4 is present at about 60-fold higher concentration than total T3. T4 acts as a prohormone, as the reservoir for the production of T3, the active hormone. The metabolic activity associated with thyroid hormone (TH) is initiated by T3 binding to specific nuclear receptors within target cells. Thyroid hormone concentrations in blood are essential tests for the assessment of thyroid function.

Steroids make up another important class of hormones. Examples of steroid hormones include estrogens, progesterone and testosterone. Estrogen is the name of a group of hormones of which there are three principle forms, estrone, estradiol and estriol. Estrogens and progesterone cause the development of the female secondary sexual characteristics and develop and maintain the reproductive function. Testosterone develops and maintains the male secondary sex characteristics, promotes growth and formation of sperm. Steroids enter target cells and bind to intracellular receptors and then cause the production of mRNA coding for proteins that manifest the changes induced by steroids.

The accurate analysis and quantfication of hormones is becoming more important. For example, estrogen and estrogen like compounds are playing an ever-increasing role in today's society through hormone replacement therapy. Also, the analysis and quantification of estrogen and estrogen-like compounds helps in the management of estrogen-related diseases, like breast cancer. In addition, the accurate analysis and quantification of T4 and T3 is an issue recognized by those skilled in the art. The presence of circulating iodothyronine-binding autoantibodies that interfere with total T4 and T3 radioimmunoassays ("RIAs") is a known phenomenon [2], [3], [4]. These autoantibodies may give falsely high, or falsely low values of thyroid hormone measurements depending on the assay separation method used, and are often in discordance with the clinical features [2], [3], [4]. Direct serum free T4 and T3 (FT4 and FT3) measurements are a way to compensate for such abnormal binding. However, technically, it is difficult to measure the free hormone concentrations since these are so low. It is easier to measure the total (free and protein-bound) thyroid hormone concentrations; total hormone concentrations are measured at nanomolar levels whereas free hormone concentrations are measured in the picomole range and to be valid, must be free from interference by the much higher total hormone concentrations.

Presently, the common methods of hormone analysis use immunoassay techniques. Table 1 lists the common hormones and the current methods for their analysis.

For example, estriol is analyzed by a radioimmunoassay utilizing radiolabelled antigen (iodine 125) in competition with unlabelled estriol in the sample, for a known amount of antibody. The assay is read using a gamma counter.

Androstenedione is analyzed using an enzyme immunoassay comprising horseradish peroxidase. Unlabeled antigen in the sample is in competition with enzyme labeled antigen for a fixed number of antibody binding sites. The assay is read using a microtitre plate enzyme immunoassay reader.

Several hormones are currently analyzed using a chemiluminescent immunoassay. For example, progesterone, testosterone, cortisol and T3 are analyzed using this method. The assay utilizes an assay specific antibody-coated bead. The assay is read using a photon counter.

However, the current immunoassays are disadvantageous for the following reasons:

(1) Immunoassays are specific to one hormone, therefore every hormone must be analyzed separately.
(2) Numerous kits must be purchased and procedures must be learned for each hormone being analyzed.
(3) Various instruments to read the results from the immunoassays must be purchased. For example, the analysis of estriol and progesterone from a sample requires both a gamma counter and a photon counter.
(4) The kits for the assays can be expensive.
(5) The current immunoassays lack specificity and may show approximately 15 fold difference In results using kits from different manufacturers [5].
(6) The procedures involve many steps and can take a significant amount of time.
(7) In the case of a radioimmunoassay, precautions are necessary because of the radioisotopes involved.

Immunoassays are notoriously unreliable with more and more literature published supporting their lack of specificity [6-13]. Table 2 shows the major differences reported by the College of American Pathologists program for proficiency Testing of thyroid hormones that clearly illustrates the difference in specificity of the various antibodies used. For example. Table 2 shows mean results between different methods reported in the College of American Pathologists Proficiency Testing (CAP PT) Program can vary by a factor of approximately 2. Some factors such as pregnancy, estrogen therapy or genetic abnormalities in protein binding have also reportedly made Immunoassay methods for T4 and T3 diagnostically unreliable [2], [3], [14], [15]. Currently serum total T4 (TT4) and total serum T3 (TT3) concentrations are most commonly measured by immunoassay methods. Recently some reports of quantitative measurement of T4 and T3 by high performance liquid chromatography (HPLC), gas chromatography mass spectrometry (GC-MS), liquid chromatography mass spectrometry (LC-MS) or tandem mass spectrometry (LC-MS/MS) were published [16-20]. All those methods required extraction, derivatization and even prior chromatographic separation that are very time consuming [21], [22].

More recently, hormones have been analysed and quantified by mass spectrometry. However, there are several disadvantages to these methods.

For example, a method of analyzing urinary testosterone and dihydrotestosterone glucuronides using electrospray tandem mass spectrometry has been described [23]. The method involves a complex system employing high testosterone and the limit of quantification was 10 ug $L^{-1}$ for dihydrotestosterone and (v) the method is complex.

Another publication discloses a method for the determination of estradiol in bovine plasma by an ion trap gas chromatography-tandem mass spectrometry technique [24]. The shortcomings include the following: (i) only one analyte was analyzed, (ii) 4 ml of plasma was required for the analysis of one analyte, (iii) the limit of detection was 5 pg $ml^{-1}$, and (iv) derivation was required because the method employs gas chromatography.

A method for analysis of 17-hydroxyprogesterone by HPLC eleotrospray ionization tandem mass spectrometry from dried blood spots has also been described [25]. However, this method analyses only one analyte at a time, and requires liquid-liquid extraction, which is laborious and time consuming, with sample extraction alone taking 50 minutes to complete.

Finally, a gas chromatography mass spectrometry method to analyze the production rates of testosterone and dihydrosterone has been disclosed [26].

TABLE 1

METHODS AND INSTRUMENTS FOR STEROID AND THYROID HORMONES [1].

| ANALYTE | Percentage of Use | Instrument | METHOD |
|---|---|---|---|
| Androstenedione | 35% | DSL solid | EIA |
| 11-Deoxycortisol | 50% | ICN Immuchem DA | RIA |
| DHEA Sulfate | 39% | DPC Immulite | ECIA |
| Estradiol | 16% | Bayer ADVIA Centaur | FIA |
| Estriol, unconjugated | 25% | DSL liquid | RIA |
| Estriol, Total | 50% | DPC Coat-a-Count | RIA |
| 17-Hydroxyprogesterone | 51% | DPC Coat-a-Count | RIA |
| Progesterone | 23% | Bayer ADVIA Centaur | CIA |
| Testosterone | 29% | Bayer ADVIA Centaur | CIA |
| Testosterone, Free | 65% | DPC Coat-a-Count | RIA |
| Aldosterone | 76% | DPC Coat-a-Count | RIA |
| Cortisol | 25% | Bayer ADVIA Centaur | CIA |
| T3 | 29% | Abbott Axsym | FPIA |
| T3, Free | 31% | Bayer ADVIA Centaur | CIA |
| T4 | 30% | Abbott Axsym | FPIA |
| T4, Free | 34% | Abbott Axsym | FPIA |

RIA: RadioImmunoassay
EIA: Enzyme Linked Immunoassay
FPIA: Fluorescence Polarization Immunoassay

TABLE 2

Problems with Immunoassays: Data acquired from CAP PT Program 2003

| Analyte | Mean CAP Result for Method Giving Lowest Value | Mean CAP Result for Method Giving Highest Value |
|---|---|---|
| Triiodothyronine (ng/dL) | 108.5 | 190.2 |
| | 364.8 | 610.1 |
| Thyroxine (ug/dL) | 5.64 | 10.09 |
| | 1.64 | 3.65 |
| | 8.73 | 13.12 |

Table 2: Problems with Immunoassays: Data acquired for samples from the CAP PT Program 2003.

SUMMARY OF THE INVENTION

The invention provides a fast and accurate method of hormone analysis and quantification using a mass spectrometer.

A plurality of hormones can be analyzed simultaneously or sequentially. The procedure allows for as little as 100 μL of a sample to be analyzed. In addition, minimal sample preparation time is required.

The invention permits the analysis of hormones in a number of complex matrices as they might be found in nature, e.g. the human body. For, example, hormone analysis can be performed on samples of blood, saliva, serum, plasma and urine.

There are several advantages to this invention:

(1) It provides a total and specific analysis for hormones in a sample. The present method allows for the analysis of many hormones simultaneously or sequentially.

(2) The procedure does not require an immunoprecipitation reaction. The majority of other methods for hormone analysis required an immunoassay. Immunoassays are expensive, specific to a particular analyte and involve several steps.

(3) The present invention requires minimal sample preparation time. For example, preparing a sample for hormone analysis can be done within 6 minutes.

(4) The procedure does not require a large sample size. A plasma or serum sample can be as small as 100 μL for thyroid hormones. The current methods for hormone analysis that utilize mass spectrometry require 4-15 mL of plasma.

(5) The invention uses simple preparation techniques that are easy to use and highly reproducible.

(6) The invention permits analysis to be performed on a variety of sample types.

(7) The invention permits the analysis of hormones In a sample of saliva or urine which permits simple sample acquisition and the remote submission of samples to a clinic for analysis. In previous other clinical methods, samples are taken by invasive means directly from the patient in a clinic.

(8) The analysis by mass spectrometry is highly accurate. In addition, the procedure of the present invention is highly reproducible.

(9) The invention permits the analysis of a wide range of hormone concentrations. In addition, the limit of detection can be fairly low.

Accordingly, there is provided a use for a mass spectrometer for simultaneously or sequentially analyzing a sample for a plurality of hormones in a fast, simple and accurate way. The sample may be, for example, serum, plasma, urine or saliva.

There is also provided a system for the fast, simple and accurate analysis of a plurality of hormones comprising:

reagents for the preparation of the sample, reagents to perform the analysis on a mass spectrometer, and a mass spectrometer to perform the analysis.

There is also provided a kit, comprising the various reagents required for simultaneously or sequentially analyzing, within a sample, a plurality of hormones, including steroid hormones, thyroid hormones and other hormones. The kit may include a standard solution of the hormones of interest, compounds as internal standards, mobile phase solutions, methods and tools for separating hormones from samples, for example HPLC columns, and quality control specimens.

There is also provided a method for the simultaneous or sequential analysis of one or more hormones comprising ionizing the hormones and analyzing the hormones by mass spectrometry.

Accordingly, there is also provided a method for the simultaneous or sequential analysis of one or more hormones comprising: obtaining a sample containing or suspected of containing one or more hormones, removing proteins from the sample, separating the hormones from the sample, ionizing the hormones and analyzing the hormones in a mass spectrometer.

Accordingly, there is also provided a method for the analysis of one or more thyroid hormones comprising: obtaining a sample containing or suspected of containing one or more thyroid hormones, removing proteins from the sample, separating the thyroid hormone from the sample, ionizing the thyroid hormones, for example by electrospray ionization, and analyzing the hormone in a mass spectrometer, preferably in the negative mode.

Accordingly, there is also provided a method for the simultaneous or sequential analysis of one or more thyroid hormones comprising, obtaining a sample containing or suspected of containing one or more thyroid hormones, removing proteins from the sample, separating the thyroid hormones from the sample, ionizing the thyroid hormone, for example by electrospray ionization, and analyzing the hormones in a mass spectrometer, preferably in the negative mode.

Accordingly, there is also provided a method for the simultaneous or sequential analysis of a plurality of thyroid hormones and a plurality of steroid hormones comprising: obtaining a sample containing or suspected of containing a plurality of hormones, removing proteins from the sample, separating the hormones from the sample, ionizng the thyroid hormones, for example, by electrospray ionization, ionizing the steroid hormones by photoionization, and analyzing the hormones in a mass spectrometer, in the negative or positive modes.

BRIEF DESCRIPTION OF THE DRAWINGS

The invention, including the best approaches known to the inventors, can be better understood with reference to the following detailed description taken in combination with the following drawings, in which.

DETAILED DESCRIPTION OF THE EXEMPLIFIED EMBODIMENT

Figure 1:
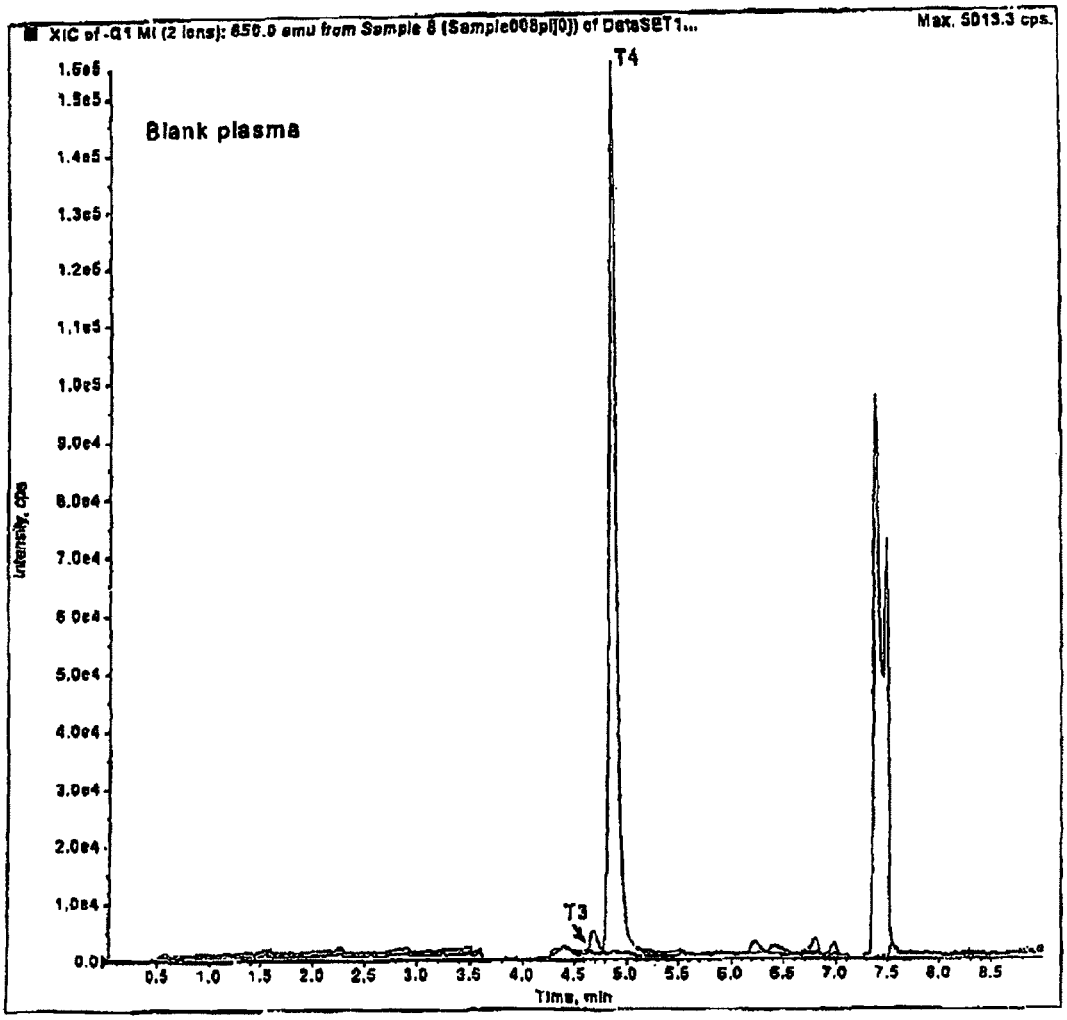
FIG. 1 is a mass spectrum of a sample of plasma containing T4 and T3.

The invention provides methods of analysis for hormones. The hormones may include:

Dehydroepiandrosterone (DHEA)
Dehydroepiandrosterone sulphate (DHEAS)
Aldosterone
Cortisol
11-Deoxycorisol
Androstenedione
Testosterone
Estradiol
17-OH Progesterone
Progesterone
Allopregnanolone
16-OH Estrone
2-OH Estrone
Estrone
Estriol
Vitamin D
thyroxine
free thyroxine
triiodothyronine
catecholamines
metanephrines
other steroid hormones
other thyroid hormones
other small peptide hormones
other amines Sample Any sample containing or suspected of containing a hormone can be used, including a sample of blood, plasma, serum, urine or saliva. The sample may contain both free and conjugated or bound hormones. A sample size of at least about 100 μL for hormones generally, or at least about 700 μL for steroid hormones, is presently preferred.

Deproteinization

The sample is de-proteinated. This can be done by conventional techniques known to those skilled in the art. For example, a sample can be de-proteinated with acetonitrile, containing internal standard, followed by vortexing and centrifugation. The internal standard may be, for example, the deuterated hormone.

Separation of Hormones from the Sample

The hormones are separated by methods known to those skilled in the art. For example, the hormones may be separated by liquid chromatography through a column. The column may be a C-18 column. The hormones are subsequently eluted from the column.

Introduction of Hormones into a Mass Spectrometer

The hormones are then introduced into a mass spectrometer. Optionally, the separation step and step of introducing the hormones into a mass spectrometer can be combined using a combined liquid chromatography spectrometry apparatus (LC/MS). This procedure is based on an online extraction of the injected sample with subsequent introduction into the mass spectrometer using a built-in switching valve.

Isotope Dilution Tandem Mass Spectrometry

Isotope dilution tandem mass spectrometry incorporates additional dilution steps that act as an internal calibration so that an independent isotopic reference material is not required. It avoids the need to measure the isotope ratio of the highly enriched spike directly, and enables the final results to be arranged as a combination of measurements that are largely insensitive to instrumental bias and drift. Consequently, it has the potential to extend the scope of application of isotope dilution tandem mass spectrometry to include analysis for which reference materials with certified isotope ratios are not available or where contamination of the instrument by the highly-enriched spike causes difficulty.

Instrumentation and Ionization Techniques

The hormones are subjected to ionization. Various ionization techniques can be used. For example, photoionization, electrospray ionization (ESI), atmospheric pressure chemical ionization (APCI), and electron capture ionization may be used. Preferably, electrospray ionization is utilized when analyzing thyroid hormones.

The following mass spectrometers can be used: any tandem-mass spectrometer, including hybrid quadrupole-linear ion trap mass spectrometers and liquid chromatography-tandem mass spectrometers such as the API 2000™ mass spectrometer the API 3000™ mass spectrometer, and the API 4000™ mass spectrometer, described in U.S. Pat. Nos. 4,121,099; 4,137,750; 4,328,420; 4,963,736; 5,179,278; 5,248,875; 5,412,208; and 5,847,386 (Applied Biosystems/MDS SCIEX, Foster City, Calif./Concord Ontario, Canada). When analyzing thyroid hormones, a spectrometer with a turbo spray ion source, such as the API 2000™ and API 3000™ mass spectrometers, is presently preferred. When analyzing FT4, the API 4000™ mass spectrometer is presently preferred.

Ionization may be performed by utilizing the mass spectrometer in the negative or the positive mode, depending on a particular analyte's tendency to give rise to a particular ion form, as is known to those skilled in the art. Typically, for thyroid hormones, the spectrometer is employed in the negative mode.

Hormones are identified on the basis of the mass to charge ratio of their molecular ions and fragment ions, as is known to those skilled in the art. When the hormones are purified by liquid chromatography, they can also be identified by their retention times.

Hormones are quantified by their intensity as determined in the mass spectrometer in counts per second. Calibration curves for known concentrations of the hormones are established for comparison.

EXAMPLES

The invention will now be demonstrated using the following examples, provided to demonstrate but not limit the embodiments of the present invention:

1. Analysis of a Sample for Thyroid Hormones

A sample of 100 μL of plasma was used. Proteins were precipitated with 150 μL of acetonitrile, capped and vortexed. The sample was then centrifuged, and 200 μL of the supernatant was injected onto a Supelco LC-18-DB™ chromatographic column equipped with Supelco Discovery C18™ guard column, coupled to a tandem mass spectrometer (LC/MS/MS). The column was washed with 20% methanol in 5 mM ammonium acetate for 3 minutes. The valve was switched and the sample was eluted in 75% to 95% methanol. The total run time was 6 minutes. Slight adjustments to the volumes, concentrations and times described can be made, as is known to those skilled in the art.

The eluant was introduced into an ion-spray ionization chamber and analyzed by API 2000™ mass spectrometer using the negative mode. The mass/charge ratios for T4 and T3 ions is 775.8 and 650 respectively. The ionization may be by electrospray using a turboionspray chamber.

This demonstrates a simple method of preparing a complex biological matrix for analysis of hormone content, and a sensitive analytical method that permits the simultaneous analysis of two hormones, T3 and T4.

2. Analysis of Thyroid Hormones Using a Methanol Gradient to Elute the Hormones

A sample of 100 μL of plasma was used. Proteins were precipitated with 150 μL of acetonitrile, containing an internal standard of deuterated $T_4$, and vortexed. The sample was centrifuged, and 200 μL of the supernatant was injected onto a C-18 column coupled to a tandem mass spectrometer (LC/MS/MS). The column was washed with 20% methanol in 5 mM ammonium acetate for 3 minutes. The valve on the column was switched and the sample was eluted in a methanol gradient of 20 to 100%. The total run time was 7 minutes. Slight adjustments to the volumes, concentrations and times described can be made by those skilled in the art.

Figure 2:
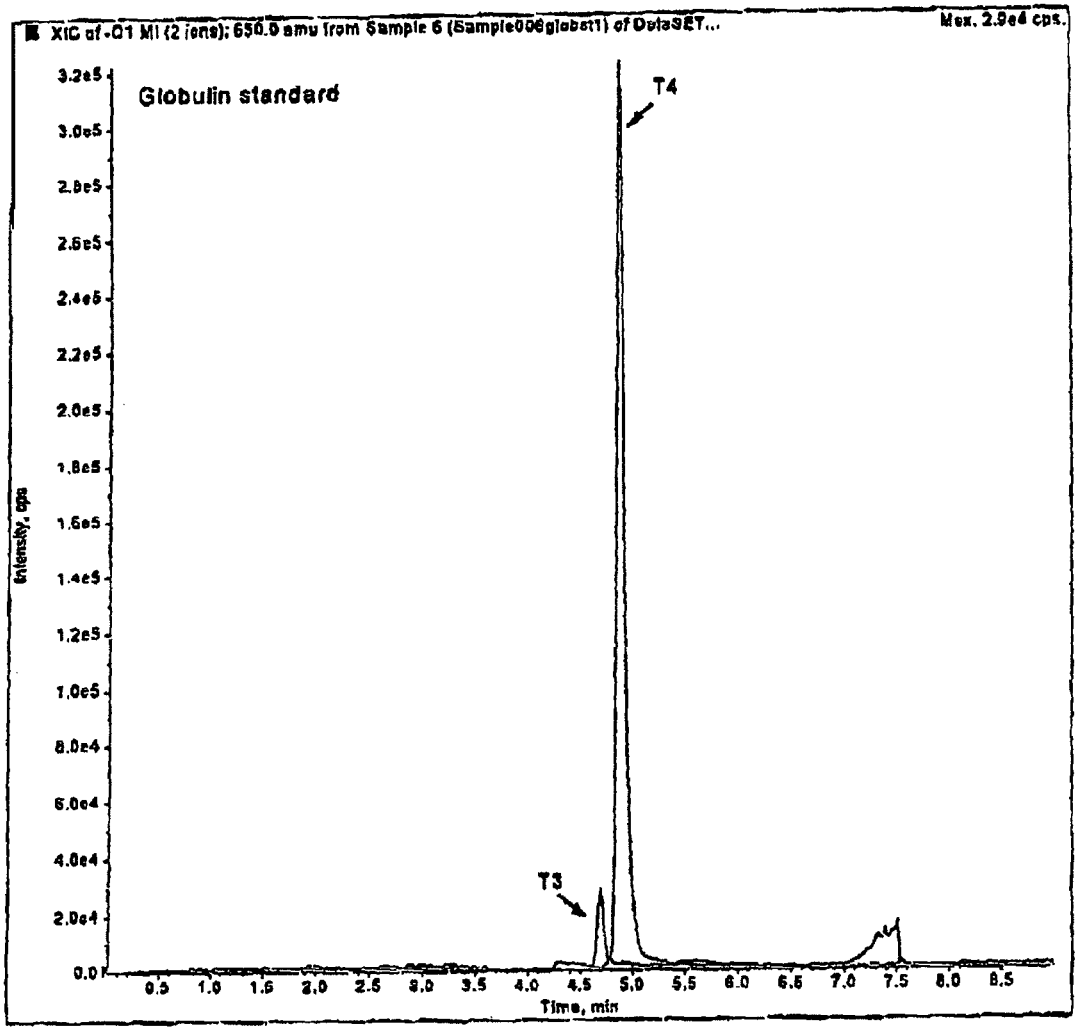
FIG. 2 is a mass spectrum of a globulin standard containing T4 and T3.

A sample of the eluant was introduced into an ion-spray ionization chamber and analyzed by an AP 2000™ mass spectrometer using the negative mode. The ionization may be by electrospray using a turboionspray chamber. See FIG. 1 and FIG. 2 for mass spectrums generated for T3 and T4.

This demonstrates a simple method of preparing a complex biological matrix for analysis of thyroid hormone content, and a sensitive analytical method that permits the simultaneous analysis of multiple hormones.

3. Analysis of Thyroid Hormones Using Isotope Dilution Tandem Mass Spectrometry

This example describes an isotope dilution tandem mass spectrometry method for the simultaneous determination of T4 and T3 in serum. The method is accurate, specific, precise (% CVs between 3.5 and 9.0), simple—requiring no extraction and only protein precipitation and fast (<7 min).

Chemicals and Reagents

Standards of T4 and T3 were purchased from Sigma (St Louis, Mo., USA). A stable deuterium-labeled internal standard, L-thyroxin-$d_2$ was synthesized according to procedures described in the literature [16]. [17] by Dr Tomas Class from the Chemistry Department at Georgetown University. HPLC grade methanol was purchased from VWR Scientific. All other chemicals were of analytical grade and purchased from Sigma.

Solutions and Standards

Stock solutions of T3, T4 and internal standard (IS) were prepared separately to obtain concentration of 1 mg/mL for each. 40% ammonium hydroxide (v/v) in methanol was used as a solvent. The analyte stock solutions were diluted with methanol to obtain the spiking solutions. The solutions were stored at 4° C. and could be used for several months. Standards for the calibration curve in the range of 0.325 to 5 ng/mL for T3 and 12.5 to 200 ng/mL for T4 were prepared by adding the analyses to 3% human γ-globulin (volume of spiking solution <2% of final volume). Quality control (QC) samples (Diagnostic Product Corp., Los Angeles, USA) at low, medium and high levels were used. A solution of 50-ng/mL $d_2$-T4 in methanol was used as the internal standard.

Sample Preparation

Serum/plasma samples were thawed at room temperature. 150 μL of IS solution was added to aliquots of 100 μL of the serum or plasma sample. After 30 seconds of vortex mixing, the samples were stored for 10 min at room temperature to allow complete protein precipitation. The samples were centrifuged for 10 min at 15,000 rpm and 100 μl of supernatant was injected into the LC-MS-MS system.

LC/MS/MS Conditions

An API 3000™ tandem mass-spectrometer (SCIEX, Toronto, Canada) equipped with turboionspray and Shimadzu HPLC system was used to perform the analysis. Negative ion multiple reaction-monitoring (MRM) mode was used. The transitions to monitor were selected at m/z 650→127 for T3, m/z 776-127 for T4, m/z 778→127 for $d_2$-T4. Nitrogen served as auxiliary, curtain and collision gas. Gas flow rates, source temperature, ion Spray voltages and collision energies were optimized for every compound by infusion of 1 μg/mL of the standard solutions in methanol at 20 μL/min and by flow-injection analysis (FIA) at LC flow rate. The main working parameters for the mass spectrometer are summarized in Table 3. Data processing was performed on Analyst 1.2 software package.

LC-MS-MS Procedure

The procedure is based on an online extraction/cleaning of the injected samples with subsequent introduction into the mass-spectrometer by using a built-in Valco switching valve. 100 μl of the sample were injected onto a Supelco LC-18DB (3.3 cm×3.0 mm, 3.0 μm ID) chromatographic column equipped with a Supelco Discovery C-18 (3.0 mm) Guard column, where it underwent cleaning with 20% (v/v) methanol in 5 mM ammonium acetate pH=4.0 at flow rate 0.8 mL/min. After 3.5 min of cleaning the switching valve was activated, the column was flushed with water/methanol gradient at flow rate 0.5 mL/min and the samples were introduced into the mass-spectrometer. The gradient parameters are shown in Table 4.

Immunoassays for T4 and T3

T4 was measured by the Dade RxL Dimension (Dade-Behring Diagnostics, Glasgow, Del.) and T3 by the DPC Immulite (Diagnostic Product Corporation, Los Angeles, Calif.) according to the manufacturer's specifications.

Results

The optimal mass spectrometer working parameters are shown in Tables 3 and 4.

Replicate sera were assayed both within-day and between-day at several concentrations. The within-day and between-day precision data is provided in Tables 5 and 6.

Recovery studies for T4 and T3 are shown in Tables 7 and 8. All results shown are the means of 8 replicates.

Figure 3:
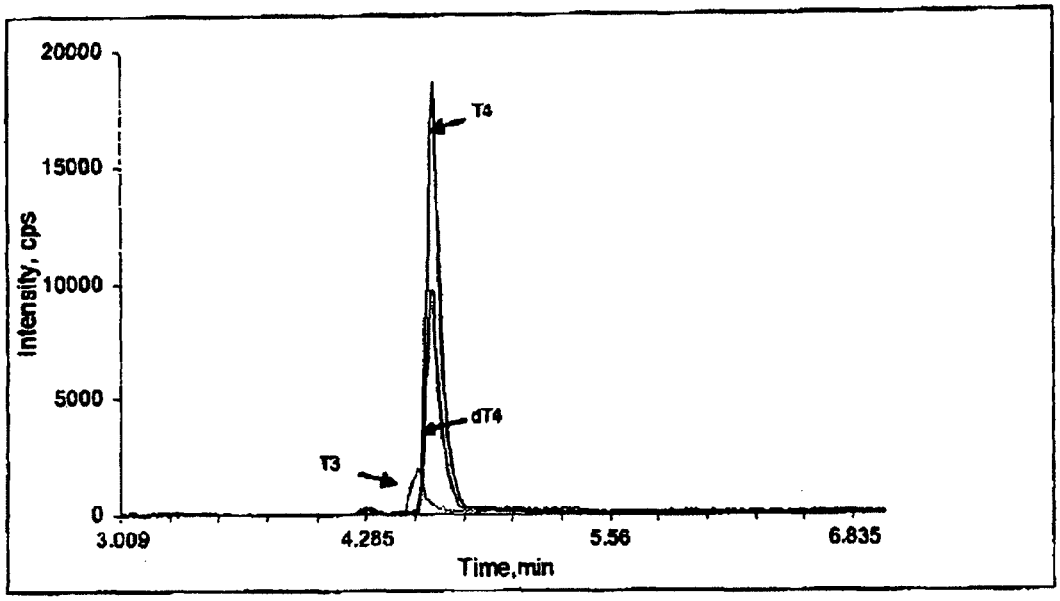
FIG. 3 is a typical tandem mass spectrometric chromatogram obtained for T4 and T3.

FIG. 3 shows a typical tandem mass spectrometric chromatogram obtained for T3 and T4.

Figure 4:
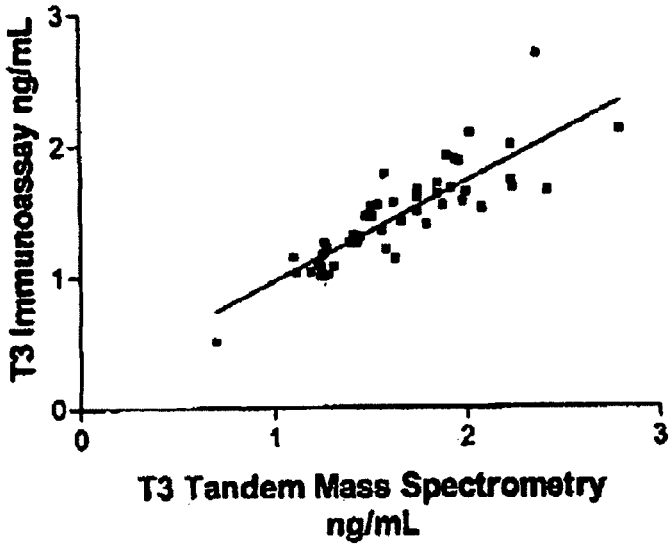
FIG. 4 is a graph showing T3 measured by Isotope Dilution Tandem Mass Spectrometry vs. Immunoassay.
Figure 5:
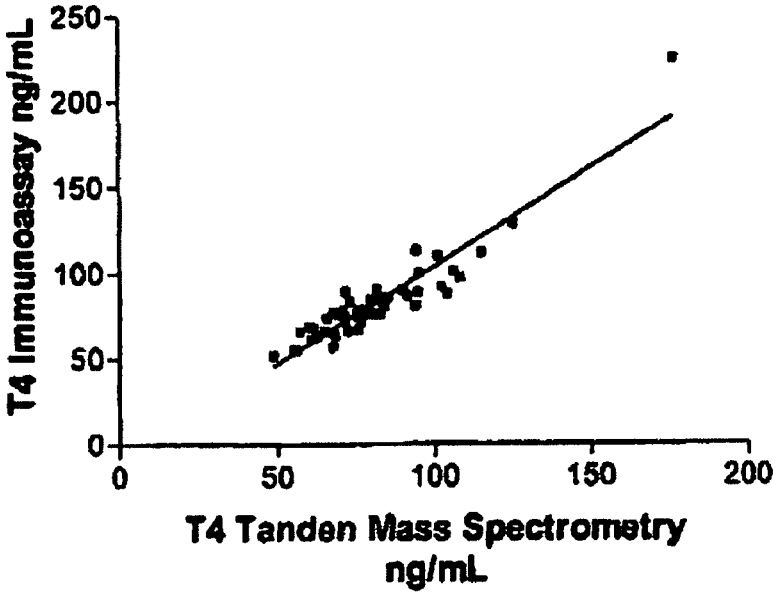
FIG. 5 is a graph showing T4 measured by Isotope Dilution Tandem Mass Spectrometry vs. Immunoassay.

Specimens were tested for T3 and T4 by both immunoassay (T3 DPC Immulite, T4 Dade Behring Dimension RxL) and by tandem mass spectrometry. Linear regression correlations (Prism) are shown in FIGS. 4 and 5.

The lower limit of quantfication of the mass spectrometry method was found to be 0.15 ng/mL for both T3 and T4. Detection limit was around 0.062 ng/mL.

Discussion

Evidence initially gleaned from both the CAP PT Program and pediatric reference ranges employing different immunoassays indicated the probability of lack of specificity for T4 and T3 immunoassay tests. To adequately assess this phenomenon we developed the isotope dilution tandem mass spectrometric method described in this example. Serum T4 and T3 detection methods have evolved through a variety of technologies since the 1950s. Radioimmunoassay (RIA) methods to detect THs were developed in the 1970s. Serum T4 and T3 concentrations are currently measured by competitive immunoassay methods (IAs) that are mostly non-isotopic and use enzymes, fluorescence or chemiluminescence molecules as signals [27]. Table 2 clearly Indicates that current IAs for T4 and T3 lack specificity and give mean results differing by a factor of approximately 2 in CAP PT programs. Total hormone assays necessitate the inclusion of a displacing agent (such as salicylate) to release the hormone from its binding proteins [28]. The displacement of hormone binding from serum proteins by such agents, together with the large sample dilution employed in modern assays, facilitates the binding of hormone to the antibody reagent.

Since T3 is ten-fold lower in concentration compared with T4 in blood it therefore presents both a technical sensitive and precision challenge despite the use of a higher specimen volume. Although a reliable high-range T3 measurement is critical for diagnosing hyperthyroidism, a reliable normal-range measurement is also important for adjusting antithyroid drug dosage and detecting hyperthyroidism in sick hospitalized patients, in whom a paradoxically normal T3 value may indicate hyperthyroidism.

The correlation coefficient for the T4 comparisons (0.931) is significantly better than for the T3 comparisons (0.084) (FIGS. 4 and 5). T3 by tandem mass spectrometry gave slightly higher results than those obtained by the DPC Immulite (FIG. 4). While this is true for children, our preliminary data for non-pregnant and pregnant women indicates a very poor correlation for T3 in both groups (r between 0.407-0.574).

The reasons for this are not clear but could include standardization issues, heterophilic antibodies etc. Of importance, we determined that reverse T3, which lacks a daughter ion of 127 m/z, therefore does not interfere in our tandem mass spectrometry method. Applying the tandem mass spectrometric method to CAP PT samples in the K/KN general ligand program again revealed that around 85% of the immunoassay methods gave means on samples which were lower than the means obtained by our tandem mass spectrometry method while 15% had higher means.

In conclusion, correlations between immunoassays and tandem mass spectrometry for T4 proved to be adequate except for the pregnant population, while the data for T3 was far less impressive especially during pregnancy. Recovery studies from several different sera using deuterated T4 as internal standard showed consistent (90-109%) recoveries for both T4 and T3 (Tables 7 and 8). The recovery differences found between samples were surprisingly larger for T4 than for T3. This indicates a lack of need to use deuterated T3 as the T3 internal standard. The isotope dilution tandem mass spectrometric method we developed is rapid (<7 min), accurate (provides the true result as has been assessed by recovery studies), specific (measures only the analyte it purports to measure), precise (low % CV) and easy to perform.

TABLE 3

Tandem mass-spectrometer working parameters

| Parameter | Value |
|---|---|
| Nebulizer gas (NEB) | 8 |
| Curtain gas (CUR) | 10 |
| Collision gas (CAD) | 6 |
| Turbolon Spray Heater gas | 7 L/min |
| Turbolon Spray (IS) voltage | 4500 V |
| Entrance Potential (EP) | 7.5 V |
| Collision cell Exit Potential (CXP) | 5 V |
| Source temperature | 450° |
| Dwell time | 250 msec |

TABLE 4

Gradient parameters

| Time (min) | Methanol (%) |
|---|---|
| 3.50 | 75 |
| 5.25 | 76 |
| 5.50 | 100 |
| 7.00 | End |

TABLE 5

| Within day precision (n = 10) | | | | | | |
|---|---|---|---|---|---|---|
| | CONTROL 1 | | | CONTROL 2 | | |
| Analyte | Mean (ng/mL) | SD | CV (%) | Mean (ng/mL) | SD | CV (%) |
| T3 | 1.04 | 0.014 | 1.36 | 2.44 | 0.077 | 3.19 |
| T4 | 24.1 | 0.437 | 1.81 | 81.2 | 1.502 | 1.85 |

TABLE 6

| Between day precision (n = 20, 1 run per day for 20 days) | | | | | | | | | |
|---|---|---|---|---|---|---|---|---|---|
| | CONTROL 1 | | | CONTROL 2 | | | CONTROL 3 | | |
| Analyte | Mean (ng/mL) | SD | CV (%) | Mean (ng/mL) | SD | CV (%) | Mean (ng/mL) | SD | CV (%) |
| T3 | 1.08 | 0.05 | 4.47 | 2.39 | 0.22 | 9.21 | 3.49 | 0.31 | 9.00 |
| T4 | 24.4 | 1.39 | 5.69 | 76.6 | 3.11 | 4.06 | 116.3 | 4.15 | 3.57 |

TABLE 7

| Recovery of added thyroxine (T4) | | | | |
|---|---|---|---|---|
| Sample # | Added (ng/mL) | Detected mean | Added amount recovered | Recovery, % |
| 1 (n = 8) | 0 | 85.9 | NA* | NA |
| | 10 | 96.7 | 10.8 | 108.0 |
| | 40 | 127.5 | 41.6 | 104.0 |
| 2 (n = 5) | 0 | 62.6 | NA | NA |
| | 10 | 72.1 | 9.5 | 95.0 |
| | 40 | 98.0 | 35.4 | 90.0 |
| 3 (n = 5) | 0 | 73.8 | NA | NA |
| | 10 | 84.7 | 10.9 | 109.0 |
| | 40 | 116 | 42.2 | 105.0 |
| 4 (n = 5) | 0 | 58.3 | NA | NA |
| | 10 | 68.0 | 9.7 | 97.0 |
| | 40 | 95.0 | 36.7 | 92.0 |

*NA—not applicable

TABLE 8

| Recovery of added triiodothyronine (T3) | | | | |
|---|---|---|---|---|
| Sample # | Added (ng/mL) | Detected mean | Added amount recovered | Recovery, % |
| 1 (n = 8) | 0 | 1.88 | NA | NA |
| | 0.25 | 2.12 | 0.24 | 96.0 |
| | 1.00 | 2.85 | 0.97 | 97.0 |
| 2 (n = 5) | 0 | 1.70 | NA | NA |
| | 0.25 | 1.96 | 0.26 | 104.0 |
| | 1.00 | 2.76 | 1.06 | 106.0 |
| 3 (n = 5) | 0 | 1.56 | NA | NA |
| | 0.25 | 1.81 | 0.25 | 100.0 |
| | 1.00 | 2.62 | 1.06 | 106.0 |
| 4 (n = 5) | 0 | 0.49 | NA | NA |
| | 0.25 | 0.74 | 0.25 | 100.0 |
| | 1.00 | 1.50 | 1.01 | 101.0 |

*NA—not applicable

4. Analysis of Thyroid Hormones and Steroid Hormones

A sample of 100 μL of plasma is used. Proteins are precipitated with 150 μL of acetonitrile and vortexed. The sample is centrifuged, and 200 μL of the supernatant is injected onto a C-18 column coupled to a tandem mass spectrometer (LC/MS/MS). The column is washed with 20% methanol in 5 mM ammonium acetate for 3 minutes. The valve on the column is switched and the sample is eluted in a methanol gradient of 20 to 100%. The total run time is 10 minutes. Slight adjustments to the volumes, concentrations and times described can be made, as is known to those skilled in the art.

A sample of the eluant is introduced into an ion-spray ionization chamber and analyzed by API 3000™ mass spectrometer using the negative mode for thyroid hormones in the sample. Steroid hormones in the sample are ionized by photoionization, with the spectrometer in the negative or positive mode. Analysis in the positive mode is typically made for DHEA, Aldosterone, Cortisol, 11-Deoxycortisol, Androstenedione, Testosterone, Estradiol, 17-OH Progesterone, Progesterone, Allopregnalone, and Vitamin D, whereas analysis in the negative mode is typically made for 16-OH Estrone, 2-OH Estrone, Estriol and DHEAS. However, it is possible to analyze any of the hormones In either positive or negative mode.

This demonstrates a simple method of preparing a complex biological matrix for analysis of possible steroid and thyroid hormone content, and a sensitive analytical method that permits the simultaneous analysis of steroid and thyroid hormones.

The results indicate that this technique, allows for the identification and characterization of low levels of thyroid hormone in human plasma and saliva.

While the above detailed description describes the exemplifying embodiments of the present invention, it should be understood that the present invention is susceptible to modifications, variations and alterations without deviating from the scope of the invention.

REFERENCES

All references listed herein are incorporated by reference in their entirety.

1. Lum S M, Nicoloff J T, Spencer C A, Kaptein E M. Peripheral tissue mechanism for maintenance of serum triiodothyronine values in a thyroxine-deficient state in man. J Clin Invest 1984; 73(2):570-575.
2. Sakata S, Nakamura S, Miura K. Autoantibodies against thyroid hormones or iodothyronine. Implications in diagnosis, thyroid function, treatment, and pathogenesis. Ann Intern Med 1985; 103(4):579-589.
3. Beck-Peccoz P. Romelli P B, Cattaneo M G, Faglia G, White E L, Barlow J W, Stockigt J R. Evaluation of free thyroxine methods in the presence of iodothyronine-binding autoantibodies. J Clin Endocrinol Metab 1984: 58(4): 736-739.
4. Klee G G. Human anti-mouse antibodies. Arch Pathol Lab Med 2000; 124(6): 921-923.
5. College of American Pathologists Proficiency Survey Report on Y-03, RAP-03 and K-06 specimens for 2003.
6. Soldin S J. Digoxin-issues and controversies. Clin Chem 1986; 32(1 Pt 1):5-12.

7. Soldin S J, Papanastasiou-Diamandi A, Heyes J, Lingwood C, Olley P. Are immunoassays for digoxin reliable? Clin Blochem 1984; 17(5):317-320.
8. Thong B, Soldin S J, Lingwood C A. Lack of specificity of current ani-digoxin antibodies, and preparation of a new, specific polyclonal antibody that recognizes the carbohydrate moiety of digoxin. Clin Chem 1985; 31(10):1625-1631.
9. Murthy J N, Davis D L, Yatscoff R W, Soldin S J. Tacrolimus metabolite cross-reactivity in different tacrolimus assays. Clin Biochem 1998; 31(8):613-617.
10. Murthy J N, Yatscoff R W, Soldin S J. Cyclosporine metabolite cross-reactivity in different cydosporine assays. Clin Blochem 1998; 31(3):159-163.
11. Shen S, Elin R J, Soldin S J. Characterization of cross reactivity by carbamazepine 10,11-epoxide with carbamazepine assays. Clin Biochem 2001; 4(2):157-158.
12. Ghoshal A K, Soldin S J. tacrolimus II assay: is it reliable at low blood concentrations? A comparison with tandem MS/MS. Clin Biochem 2002: 35(5): 389-392.
13. Soldin S J, Steele B W, Witte D L, Wang E. Elin R J. Lack of specificity of cyclosporine immunoassays. Results of a College of American Pathologists Study. Arch Pathol Lab Med 2003; 127(1):19-22.
14. Despres N. Grant A M. Antibody interference in thyroid assays: a potential for clinical misinformation. Clin Chem 1998; 44(3):440-454.
15. Same D H, Refetoff S. Nelson J C, Linarelli L G. A new inherited abnormality of thyroxine-binding globulin (TBG-San Diego) with decreased affinity for thyroxine and triiodothyronine. J Clin Endocrinol Metab 1989; 68(1): 114-119.
16. Burman K D, Bongiovanni R. Garis R K, Wartofsky L. Boehm T M. Measurement of serum T4 concentration by high performance liquid chromatography. J Clin Endocrinol Metab, 1981; 53(5): 909-912.
17. Tai S S, Sniegoski L T, Welch M J. Candidate reference method for total thyroxine in human serum; use of isotope-dilution liquid chromatography-mass spectrometry with electrospray ionization. Clin Chem 2002: 48(4):637-642.
18. Thienpont L M, De Brabandere V I, Stockl D, De Leenheer A P. Development of a new method for the determination of thyroxine in serum based on isotope dilution gas chromatography mass spectrometry. Biol Mass Spectrom 1994; 23(8): 475-482.
19. Thienpont L M, Fierens C, De Leenheer A P, Przywara L. Isotope dilution-gas chromatography/mass spectrometry and liquid chromatography/electrospray ionization-tandem mass spectrometry for the determination of triiodo-L-thyronine in serum. Rapid Commun Mass Spectrom 1999; 13(19): 1924-1931.
20. De Brabandere V I, Hou P, Stockl D, Thienpont L M, De Leenheer A P. Isotope dilution-liquid chromatography/electrospray ionization-tandem mass spectrometry for the determination of serum thyroxine as a potential reference method. Rapid Commun Mass Spectrom 1998; 12(16): 1099-1103.
21. Ramsden, D. B. and M. J. Farmer, Development of a gas chromatographic selected ion monitoring assay for thyroxine (T4) in human serum. Biomed Mass Spectrom 1984; 11(8):421-427.
22. Nishinaga A, Cahnmann H J, Kon H. Matsuura T. Model reactions for the biosynthesis of thyroxine. XII. The nature of a thyroxine precursor formed in the synthesis of thyroxine from diiodotyrosine and its keto acid analog. Biochemistry 1968; 7(1):388-397.
23. Choi M H, Kim, J N. Chung B C. Rapid HPLC-Electrospray Tandem Mass Spectrometric Assay for Urinary Testosterone and Dihydrosterone Glucuronides from Patients with Benign Prostate Hyperplasia. Clin Chem 2003;49(2): 22-325.
24. Biancotto G, Angeletti R, Traldi P. Silvestri M S, Guidugli F. Determinaton of 17β-Estradiol in Bovine Plasma: Development of a Highly Sensitive Technique by Ion Trap Gas Chromatography-Tandem Mass Spectrometry Using Negative Ion Chemical Ionization. J Mass Spectrom 2002; 37: 1226-1271.
25. Lai C C, Tsai C H, Tsai F J, Wu J Y, Lin W D, Lee C C. Rapid Screening Assay of Congenital Adrenal Hyperplasia by Measuring 17α-Hydroxy-progesterone with High-Performance Liquid Chromatography/Electrospray Ionization Tandem Mass Spectrometry From Dried Blood Spots. J Clin Lab Anal 2002;16: 20-25.
26. Vierhapper H, Nowotny P, Waldausl W. Reduced Production Rates of Testosterone and Dihydrosterone in Healthy Men Treated with Rosiglitazone. Metabolism 2000;52(2): 230-232.
27. Nelson J C, Wilcox R B. Analytical performance of free and total thyroxine assays. Clin Chem 1996; 42(1):146-154.
28. Evans S E, Burr W A, Hogan T C. A reassessment of 8-anilino-1-naphthalene sulphonic acid as a thyroxine binding inhibitor in the radioimmunoassay of thyroxine. Ann Clin Biochem 1977; 14(6):330-334.

What is claimed is:

1. A method for mass spectrometric analysis of a [100 μL] sample comprising one or more thyroid hormones, the method consisting *essentially* of the steps of: (a) providing a sample comprising one or more thyroid hormones[, wherein the sample is approximately 100 μL]; (b) deproteinating the sample; (c) separating the one or more thyroid hormones from the sample; and (d) analyzing the one or more thyroid hormones using a mass spectrometer.

2. The method according to claim 1 wherein the one or more thyroid hormones are selected from the group consisting of T3 and T4.

3. The method according to claim 1 wherein the sample comprising one or more thyroid hormones is obtained from a biological sample selected from the group consisting of blood, plasma, serum, urine and saliva.

4. The method of claim 3 wherein the biological sample is blood.

5. The method of claim 3 wherein the biological sample is plasma.

6. The method of claim 3 wherein the biological sample is serum.

7. The method of claim 3 wherein the biological sample is urine.

8. The method of claim 3 wherein the biological sample is saliva.

9. The method according to claim 1 wherein said step of deproteinating the sample comprises:

(a) adding acetonitrile, containing internal standards;

(b) vortexing the sample; and (c) subjecting the sample to centrifugation.

10. The method according to claim 1 wherein said step of deproteinating the sample comprises subjecting the sample to precipitation with an agent containing internal standards, said agent selected from the group consisting of methanol, ethanol and salt.

11. The method according to claim 1 wherein said step of separating the one or more thyroid hormones from the sample comprises introducing the sample to a liquid chromatography apparatus comprising a column and subsequently eluting the thyroid hormones from the column.

12. The method according to claim 11 wherein said step of separating the one or more thyroid hormones from the sample comprises the use of a C-18 column.

13. The method according to claim 1 wherein said step of separating the one or more thyroid hormones from the sample comprises the use of a combined liquid chromatography spectrometry apparatus.

14. The method according to claim 13 wherein the one or more thyroid hormones are introduced into a mass spectrometer directly after being separated from the sample by way of an on-line extraction and use of a built-in switch valve.

15. The method according to claim 1 wherein the mass spectrometer is a liquid chromatography-tandem-mass spectrometer.

16. The method according to claim 15 wherein the liquid chromatography-tandem mass spectrometer is equipped with an electrospray ionization source.

17. The method according to claim 1 wherein said step of analyzing the one or more thyroid hormones using a mass spectrometer comprises an ionization technique selected from the group consisting of photoionization, electrospray ionization, atmospheric pressure chemical ionization, and electron capture ionization.

18. The method according to claim 17 wherein said ionization technique is electrospray ionization.

19. The method according to claim 17 wherein said ionization is performed in positive mode.

20. The method according to claim 17 wherein said ionization is performed in negative mode.

21. The method according to claim 1 wherein said step of analyzing the one or more thyroid hormones using a mass spectrometer comprises multiple reaction monitoring.

22. The method according to claim 1 wherein said step of analyzing the one or more thyroid hormones using a mass spectrometer comprises selected ion monitoring.

23. The method according to claim 1 wherein the sample comprises a plurality of thyroid hormones and they are analyzed simultaneously.

24. The method according to claim 1 wherein the sample comprises a plurality of thyroid hormones and they are analyzed sequentially.

25. The method according to claim 1 wherein the sample is analyzed by isotope dilution tandem mass spectrometry.

26. A method of instructing an analysis of a sample comprising one or more thyroid hormones, the method comprising providing instructions to prepare the sample according to steps (b) and (c) of claim 1 and analyze the one or more thyroid hormones from the sample according to step (d) of claim 1.

27. A system for the mass spectrometric analysis of a sample comprising one or more thyroid hormones, [and] *wherein* the sample is [approximately] *at least about* 100 μL, *said system* comprising:

(a) reagents for deproteinating the sample, including internal standards;

(b) reagents for analyzing the sample comprising one or more thyroid hormones using a mass spectrometer; and (c) a mass spectrometer.

28. The system according to claim 27 wherein the mass spectrometer is a liquid chromatography-tandem mass spectrometer.

29. A kit for use in mass spectrometric analysis of a sample comprising one or more thyroid hormones, and wherein the sample is [approximately] *at least about* 100 μL, *said kit* comprising:

(a) reagents for deproteinating the sample comprising one or more thyroid hormones, including internal standards;

(b) reagents for separating the one or more thyroid hormones from the sample comprising one or more thyroid hormones;

(c) reagents for analyzing the one or more thyroid hormones using a mass spectrometer;

(d) a solution of one or more thyroid hormones; and (e) instructions for analyzing the one or more thyroid hormones using a mass spectrometer, wherein the analysis does not involve an extraction step comprising evaporation and redissolving the extracted thyroid hormone, and the analysis is done in less than an hour.

30. The kit according to claim 29 further comprising:

(a) mobile phase solutions;

(b) a chromatography column; and (c) a quality control specimen.

31. [Use of] *A method for using* a mass spectrometer for sequentially or simultaneously analyzing a [100 uL] sample comprising or suspected of comprising a plurality of thyroid hormones, wherein the [use] *method* consists of the steps of:

(a) providing a sample comprising or suspected of comprising a plurality of thyroid hormone, wherein the sample is [approximately] *at least about* 100 μL;

(b) deproteinating the sample;

(c) separating the plurality of thyroid hormones from the sample; and (d) analyzing the plurality of thyroid hormones using a mass spectrometer.

32. The [use] *method* according to claim 31 wherein the mass spectrometer is a liquid chromatography-tandem mass spectrometer.

33. The method of any one of claims 1 wherein the mass spectrometer is an API 2000™ mass spectrometer.

34. The method of any one of claims 1 wherein the mass spectrometer is an API 3000™ mass spectrometer.

*35. A method for mass spectrometric analysis of a sample comprising one or more thyroid hormones, the method comprising the steps of:*

*(a) providing a sample comprising one or more thyroid hormones, wherein the sample is at least about 100 μL;*

*(b) deproteinating the sample;*

*(c) separating the one or more thyroid hormones from the sample; and*

*(d) analyzing the one or more thyroid hormones using a mass spectrometer.*

*36. The method according to claim 35 wherein the one or more thyroid hormones are selected from the group consisting of T3 and T4.*

*37. The method according to claim 35 wherein the sample comprising one or more thyroid hormones is obtained from a biological sample selected from the group consisting of blood, plasma, serum, urine and saliva.*

*38. The method of claim 37 wherein the biological sample is blood.*

*39. The method of claim 37 wherein the biological sample is plasma.*

*40. The method of claim 37 wherein the biological sample is serum.*

*41. The method of claim 37 wherein the biological sample is urine.*

*42. The method of claim 37 wherein the biological sample is saliva.*

*43. The method according to claim 35 wherein said step of deproteinating the sample comprises:*

*(a) adding acetonitrile, containing internal standards;*

*(b) vortexing the sample; and*

*(c) subjecting the sample to centrifugation.*

*44. The method according to claim 35 wherein said step of deproteinating the sample comprises subjecting the sample to precipitation with an agent containing internal standards, said agent selected from the group consisting of methanol, ethanol and salt.*

*45. The method according to claim 35 wherein said step of separating the one or more thyroid hormones from the sample comprises introducing the sample to a liquid chromatography apparatus comprising a column and subsequently eluting the thyroid hormones from the column.*

*46. The method according to claim 45 wherein said step of separating the one or more thyroid hormones from the sample comprises the use of a C-18 column.*

*47. The method according to claim 35 wherein said step of separating the one or more thyroid hormones from the sample comprises the use of a combined liquid chromatography spectrometry apparatus.*

*48. The method according to claim 47 wherein the one or more thyroid hormones are introduced into a mass spectrometer directly after being separated from the sample by way of an on-line extraction and use of a built-in switch valve.*

*49. The method according to claim 35 wherein the mass spectrometer is a liquid chromatography-tandem-mass spectrometer.*

*50. The method according to claim 49 wherein the liquid chromatography-tandem mass spectrometer is equipped with an electrospray ionization source.*

*51. The method according to claim 35 wherein said step of analyzing the one or more thyroid hormones using a mass spectrometer comprises an ionization technique selected from the group consisting of photoionization, electrospray ionization, atmospheric pressure chemical ionization, and electron capture ionization.*

*52. The method according to claim 51 wherein said ionization technique is electrospray ionization.*

*53. The method according to claim 51 wherein said ionization is performed in positive mode.*

*54. The method according to claim 51 wherein said ionization is performed in negative mode.*

*55. The method according to claim 35 wherein said step of analyzing the one or more thyroid hormones using a mass spectrometer comprises multiple reaction monitoring.*

*56. The method according to claim 35 wherein said step of analyzing the one or more thyroid hormones using a mass spectrometer comprises selected ion monitoring.*

*57. The method according to claim 35 wherein the sample comprises a plurality of thyroid hormones and they are analyzed simultaneously.*

*58. The method according to claim 35 wherein the sample comprises a plurality of thyroid hormones and they are analyzed sequentially.*

*59. The method according to claim 35 wherein the sample is analyzed by isotope dilution tandem mass spectrometry.*

*60. A method of instructing an analysis of a sample comprising one or more thyroid hormones, the method comprising providing instructions to prepare the sample according to steps (b) and (c) of claim 35 and analyze the one or more thyroid hormones from the sample according to step (d) of claim 35.*

* * * * *